US00PP23362P2

(12) United States Plant Patent
Klemm et al.

(10) Patent No.: US PP23,362 P2
(45) Date of Patent: Jan. 29, 2013

(54) CARNATION PLANT NAMED 'KLEDG11142'

(50) Latin Name: *Dianthus allwoodii*
Varietal Denomination: KLEDG11142

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 54 days.

(21) Appl. No.: 13/135,739

(22) Filed: Jul. 14, 2011

(51) Int. Cl.
*A01H 5/00* (2006.01)

(52) U.S. Cl. ..... Plt./273

(58) Field of Classification Search ..... Plt./276, Plt./277, 273
See application file for complete search history.

*Primary Examiner* — Kent L Bell
(74) *Attorney, Agent, or Firm* — Jondle & Associates, P.C.

(57) ABSTRACT

A new variety of carnation named 'KLEDG11142' particularly characterized by its pink purple flowers, very early flowering and good medium strong growth habit with good branching, is disclosed.

1 Drawing Sheet

Genus and species: *Dianthus allwoodii.*
Variety denomination: 'KLEDG11142'.

BACKGROUND OF THE NEW PLANT

The present invention comprises a new and distinct variety of carnation, botanically known as *Dianthus caryophyllus*, and hereinafter referred to by the variety name 'KLEDG11142'. The new variety is the result of a cross conducted in July 2006 in Stuttgart, Germany between the proprietary female parent carnation plant, an unnamed plant of *Dianthus allwoodii* (unpatented) and the proprietary male parent, 'DCP 06 030' (unpatented). A single plant selection was subsequently chosen for further evaluation and for asexual propagation. The new variety was first propagated via vegetative cuttings in June 2007 in Stuttgart, Germany and has been asexually reproduced repeatedly by vegetative cuttings in Stuttgart, Germany for approximately six to seven generations. 'KLEDG11142' has been found to retain its distinctive characteristics through successive asexual propagations via vegetative cuttings.

'KLEDG11142' has not been made publicly available or sold more than one year prior to the filing date of this application.

SUMMARY OF THE INVENTION

The following are the most outstanding and distinguishing characteristics of this new variety when grown under normal horticultural practices in a greenhouse in Stuttgart, Germany.

1. Good medium strong growth habit with good branching;
2. Pink purple flowers; and
3. Very early flowering.

DESCRIPTION OF THE PHOTOGRAPH

This new carnation plant is illustrated by the accompanying photograph which shows the flowers and foliage of the plant. The colors shown are as true as can be reasonably obtained by conventional photographic procedures. The photograph was taken in April 2010 of a 5-month-old plant grown from rooted cuttings in a 10 centimeter pot in a glass-covered greenhouse in Stuttgart, Germany under conditions which approximate those generally used in horticultural practice.

DESCRIPTION OF THE NEW VARIETY

The following detailed descriptions set forth the distinctive characteristics of 'KLEDG11142'. The data which define these characteristics were collected from asexual reproductions carried out in Stuttgart, Germany. The plant history was taken in Spring 2010 on 5-month-old plants in 10 centimeter pots that were pinched once at week 45 and grown in a glass-covered greenhouse. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Caryophyllaceae.
- *Genus and species.*—*Dianthus caryophyllus.*
- *Common name.*—Carnation.

Parentage:
- *Female parent.*—The proprietary carnation an unnamed plant of *Dianthus allwoodii* (unpatented).
- *Male parent.*—The proprietary carnation 'DCP 06 030' (unpatented).

Plant:
- *Form.*—Potted plant.
- *Habit.*—Upright.
- *Height (from top of soil).*—12.0 cm to 16.0 cm.
- *Width (spread).*—12.0 cm to 14.0 cm.
- *Life cycle.*—Perennial.
- *Flowering habit.*—Continuous.
- *Time to produce a finished flowering plant.*—4 months.
- *Propagation type.*—Vegetative cuttings.
- *Time to initiate roots.*—18 days.
- *Root description.*—Fine; RHS NN155C (White).
- *Temperature tolerances.*—+30° C. to −15° C.

Branches:
- *Strength.*—Medium.
- *Quantity per plant.*—10 to 15.
- *Color.*—RHS 137A.

*Length.*—5.0 cm to 7.0 cm.
*Diameter.*—0.5 cm.
*Internode length.*—0.2 cm to 0.4 cm.
*Texture.*—Smooth.

Leaves:
*Arrangement.*—Opposite.
*Shape.*—Lanceolate.
*Apex.*—Acute.
*Base.*—Obtuse.
*Margin.*—Entire.
*Color.*—Immature leaf (both upper and lower surfaces): RHS 137B. Mature leaf: Upper surface: RHS 137A. Lower surface: RHS 137B.
*Length.*—3.0 cm to 7.0 cm.
*Width.*—0.3 cm to 0.4 cm.
*Texture.*—Smooth.
*Venation pattern.*—Pinnate.
*Venation color* (*both surfaces*).—RHS 137C.
*Petioles.*—Absent.

Flowers:
*Blooming habit.*—Small sprays.
*Flower type.*—Double.
*Flowering season.*—Early Spring to late Autumn.
*Lastingness of individual flowers on the plant.*—10 days.
*Width.*—3.5 cm.
*Depth.*—1.5 cm.
*Shape.*—Round.
*Fragrance.*—Present.
*Number of flowers per plant.*—6 to 8.

Flower buds:
*Color.*—RHS 137C.
*Shape.*—Elliptic.
*Length.*—0.6 cm to 1.0 cm.
*Diameter.*—0.5 cm to 0.7 cm.

Petals:
*Arrangement.*—Arranged in several whorls.
*Quantity* (*per flower*).—Greater than 20.
*Shape.*—Spoon-shaped.
*Apex.*—Obtuse.
*Margin.*—Serrate.
*Base.*—Acute.
*Length.*—1.5 cm to 1.7 cm.
*Width.*—1.5 cm.
*Color.*—When opening: Upper surface: RHS 64A. Lower surface: RHS 64B. When fully opened: Upper surface: RHS 64B to RHS 64C. Lower surface: RHS 64C.
*Texture* (*both surfaces*).—Smooth.

Sepals:
*Calyx.*—Form: Cylinder vase. Length: 1.2 cm. Width: 0.6 cm.
*Arrangement.*—Fused.
*Quantity* (*per flower*).—4 to 5.
*Shape.*—Elliptic.
*Apex.*—Acute.
*Base.*—Obtuse.
*Margin.*—Smooth.
*Length.*—0.6 cm.
*Width.*—0.4 cm.
*Color* (*both surfaces*).—RHS 137B.
*Texture* (*both surfaces*).—Smooth.

Peduncle:
*Length.*—8.0 cm to 12.0 cm.
*Diameter.*—0.3 cm.
*Texture.*—Smooth.

Reproductive organs:
*Pistils.*—Quantity: 1. Stigma color: RHS 64A to RHS 64D and RHS 65A to RHS 65D. Ovary color: RHS 144D.
*Stamens.*—Quantity: Moderate. Filament: Length: 0.5 cm to 1.0 cm. Color: RHS 65D. Anther color: RHS 65A. Pollen: Amount: Moderate. Color: RHS 65B.

Fruit and seed set: None observed.

Disease and insect resistance: No particular resistance or susceptibility to common carnation diseases or insect pests has been observed.

COMPARISON WITH PARENTAL VARIETIES

'KLEDG11142' differs from the female parent, the proprietary carnation plant, an unnamed plant of *Dianthus allwoodii* (unpatented), in that 'KLEDG11142' has pink purple double flowers, while the unnamed plant of *Dianthus allwoodii* has light pink semi-double flowers.

'KLEDG11142' differs from the male parent, the proprietary carnation plant 'DCP 06 030' (unpatented), in that 'KLEDG11142' has pink purple flowers and a compact growth habit, while 'DCP 06 030' has dark purple flowers and a stronger growth habit. Additionally, 'KLEDG11142' has small leaves while 'DPC 06 030' has wide leaves.

We claim:

1. A new and distinct variety of carnation plant named 'KLEDG11142' as shown and described herein.

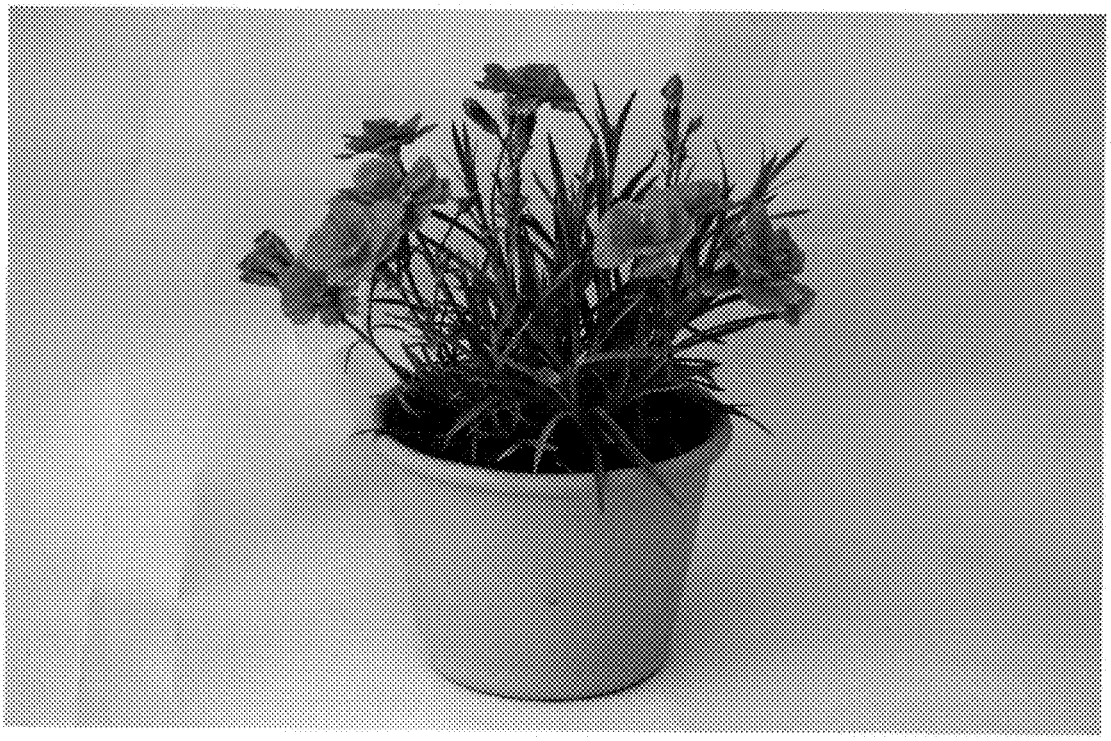

* * * * *